US007403017B2

(12) United States Patent
Hodges et al.

(10) Patent No.: US 7,403,017 B2
(45) Date of Patent: Jul. 22, 2008

(54) METHODS OF MEASURING BARRIER FORMATION

(75) Inventors: Alastair McIndoe Hodges, Blackburn South (AU); Ronald Christopher Chatelier, Bayswater (AU); Garry Chambers, Vermont (AU)

(73) Assignee: Universal Biosensors PTY Limited, Mount Waverly Vic (AU)

( * ) Notice: Subject to any disclaimer, the term of this patent is extended or adjusted under 35 U.S.C. 154(b) by 0 days.

(21) Appl. No.: 10/541,812

(22) PCT Filed: Jan. 16, 2004

(86) PCT No.: PCT/AU2004/000048

§ 371 (c)(1),
(2), (4) Date: Apr. 14, 2006

(87) PCT Pub. No.: WO2004/065951

PCT Pub. Date: Aug. 5, 2004

(65) Prior Publication Data
US 2006/0237332 A1 Oct. 26, 2006

(30) Foreign Application Priority Data
Jan. 20, 2003 (AU) .............................. 2003900285

(51) Int. Cl.
*G01N 27/02* (2006.01)
(52) U.S. Cl. ....................... 324/444; 324/469
(58) Field of Classification Search ...................... None
See application file for complete search history.

(56) References Cited
U.S. PATENT DOCUMENTS 4,319,194 A 3/1982 Cardinal et al.
4,591,793 A * 5/1986 Freilich ..................... 324/446
6,475,372 B1 11/2002 Ohara et al.
2003/0119208 A1 6/2003 Yoon et al.

FOREIGN PATENT DOCUMENTS

| DE | 3813437 | 11/1989 |
|----|---------|---------|
| DE | 19917052 | 10/2000 |
| WO | WO 97/41425 | 11/1997 |
| WO | WO 98/39643 | 9/1998 |
| WO | WO 99/64847 | 12/1999 |
| WO | WO 00/52456 | 9/2000 |
| WO | WO 01/27626 | 4/2001 |
| WO | WO 02/48707 | 6/2002 |

* cited by examiner

*Primary Examiner*—Jon P Weber
*Assistant Examiner*—Bin Shen
(74) *Attorney, Agent, or Firm*—Venable LLP

(57) ABSTRACT

There is disclosed a method of measuring formation of a barrier to restrict or reduce movement of an electroactive species. The method comprises providing an electrochemical cell having a working electrode and a counter electrode spaced from the working electrode, providing a subject component, a testing component and at least one electroactive species within the cell, the subject and testing components being intended to cause the formation of a barrier to restrict or reduce movement of an electroactive species, applying a potential between the working electrode and the counter electrode sufficient to produce a current proportional to the concentration of the electroactive species being measured, and measuring the current at the working electrode to obtain a measure of the formation of the barrier to restrict or reduce movement of the electroactive species.

20 Claims, 2 Drawing Sheets

METHODS OF MEASURING BARRIER FORMATION

This application is a national stage application of, and claims priority under 35 U.S.C. § 120 to, PCT Application PCT/AU04/00048 filed Jan. 16, 2004, which claims foreign priority to AU 2003900285 filed Jan. 20, 2003.

FIELD OF THE INVENTION

The present invention relates to an electrochemical method of measuring the formation of a barrier to restrict or reduce movement of an electroactive species which has particular application to detecting agglutination. An exemplary application of the invention is in antigen detection techniques, for example, in the analysis of whole blood for blood type.

BACKGROUND TO THE INVENTION

In the prior art, a typical way of assessing the presence of an antigen in a liquid sample is to place the sample in contact with antibodies to the antigen such that when the antibodies bind to the antigen an agglutination of species in the sample occurs. The agglutination is then assessed by optical methods, for example examining optical density, turbidity or light scattering of the sample.

For example, U.S. Pat. No. 6,330,058 discloses a method where the optical density spectrum over a predetermined wavelength range is used to arrive at an agglutination index for the sample. U.S. Pat. No. 5,256,376 also discloses a photometric technique for measuring agglutination by measuring optical density profiles together with an apparatus for use with a centrifuge to carry out the method.

Agglutination tests can be either qualitative, where only the presence or absence of the analyte is detected, or quantitative where the degree of agglutination that has occurred corresponds to a particular level of the analyte. In the prior art the assessment of the agglutination occurring has been performed visually, by using scattered light to measure the solution turbidity or by measuring optical density or the like. These visual techniques, while simple are semi-quantitative at best and open to user error, whereas the optical density or scattering techniques, while more quantitative and less prone to user error, require relatively expensive and complex equipment to be performed.

The present invention seeks to provide an alternative to these prior art techniques.

SUMMARY OF THE INVENTION

In a first aspect, the present invention provides a method of measuring formation of a barrier to restrict or reduce movement of an electroactive species in a sample, the method involving:

providing an electrochemical cell having a working electrode and a counter electrode spaced from the working electrode;

providing a subject component, a testing component and at least one electroactive species within the cell, the subject and testing components being intended to cause the formation of a barrier to restrict or reduce movement of an electroactive species;

applying a potential between the working electrode and the counter electrode sufficient to produce a current related to the rate of mass transport of the electroactive species being measured to the working electrode; and measuring the current at the working electrode to obtain a measure of the formation of the barrier to restrict or reduce movement of the electroactive species.

Preferably, the formation of a barrier is caused by agglutination.

In some embodiments, the method involves applying a potential sufficient to maintain the concentration of the electroactive species at the working electrode.

In a preferred embodiment, the invention involves measuring the current at a first time before significant barrier formation is expected to occur in the cell and measuring the current again at a second time by which significant barrier formation is expected to occur, and using the difference in measured current to obtain a measure of barrier formation.

In a preferred embodiment, the first time is a time when the change in a barrier formation measuring parameter is less than about 20% of the total change in that parameter when the barrier is fully formed in the sample and more preferably less than about 10% of the total change in that parameter.

In a preferred embodiment, the second time is a time when the change in the agglutination measuring parameter is more than about 50% of the total change in that parameter when the barrier is fully formed in the sample and more preferably more than about 70% of the total change.

In practice these times can be determined by considering the range of barrier formation kinetics possible over the range of samples and test conditions to which the device is to be applied and picking times suitable for the whole range. Alternatively, by assessing the rate of change of the barrier formation measuring parameter over time, suitable times can be obtained for each individual test.

As would be apparent to one skilled in the art the rate of change of the barrier formation measuring parameter itself could also be used as a measure of the presence or absence or concentration of the test species of interest.

The difference in measured current may be used to obtain a measure of the diffusion coefficient of the electroactive species to thereby obtain a measure of barrier formation. The difference in measured current may also be used to obtain a measure of the change in diffusion coefficient to thereby obtain a measure of barrier formation.

The testing component, the subject component and the electroactive species may be provided within the cell in a number of different ways.

Typically, the method will involve providing the subject component by placing a liquid sample containing the subject component into the cell.

In some embodiments the method will involve providing the testing component by introducing the testing component to the liquid sample before the liquid sample is placed in the cell.

In other embodiments, the testing component will be provided into the cell before the liquid sample is introduced. For example, the testing component may be stored in the cell by drying the testing component into the cell.

The electroactive species may be provided by the barrier formation reaction or another reaction between the testing component and the subject component.

Alternatively, the electroactive species may be provided by the testing component. In a further alternative, the electroactive species may be provided independently of the testing and subject components.

In one preferred embodiment, where the electroactive species is provided by the barrier formation reaction, the method involves providing two electrodes which can act as the working electrode and the testing component is provided close to or at one of the two electrodes, the method further involving varying the applied potential or current measuring circuit connections in order to switch between said working electrodes, and measuring the current at both working electrodes to thereby obtain a measure of barrier formation.

In some embodiments the measured current may be used to obtain a measure of charge which is used to obtain the measure of barrier formation.

The invention also provides a method of determining whether a target component is present in a subject component, comprising:

providing an electrochemical cell having a working electrode and a counter electrode spaced from the working electrode;

providing a subject component which may or may not comprise a target component, a testing component and at least one electroactive species within the cell, the subject and testing components being intended to cause the formation of a barrier to restrict or reduce movement of an electroactive species when the target component is present;

applying a potential between the working electrode and the counter electrode sufficient to produce a current related to the mass transport of the electroactive species being measured to the working electrode; and measuring the current at the working electrode to determine whether a barrier is formed which restricts or reduces movement of the electroactive species, to thereby determine whether said target component is present in said subject component.

The invention also extends to an apparatus for measuring a formation of a barrier to restrict or reduce movement of an electroactive species having:

an electrochemical cell having a working electrode and a counter electrode spaced from the working electrode, the electrochemical cell being adapted to receive a subject component, a testing component and at least one electroactive species within the cell, the subject and testing components being intended to cause the formation of a barrier to restrict or reduce movement of an electroactive species;

an electric power source for applying a potential between the working electrode and the counter electrode sufficient to produce a current related to the mass transport of the electroactive species being measured to the working electrode;

an ammeter for measuring the current at the working electrode; and barrier formation measurement means for determining a measure of the formation of the barrier from the measured current.

Preferably, the barrier formation measurement means is an agglutination measurement means for determining a measure of agglutination.

The electrochemical cell of the apparatus may include a separate reference electrode. Alternatively, the counter electrode may be a counter/reference electrode.

Further constructional details of the apparatus as well as additional features of the method of the present invention will become apparent from the following detailed description of the invention.

DETAILED DESCRIPTION OF THE INVENTION

Figure 1A:
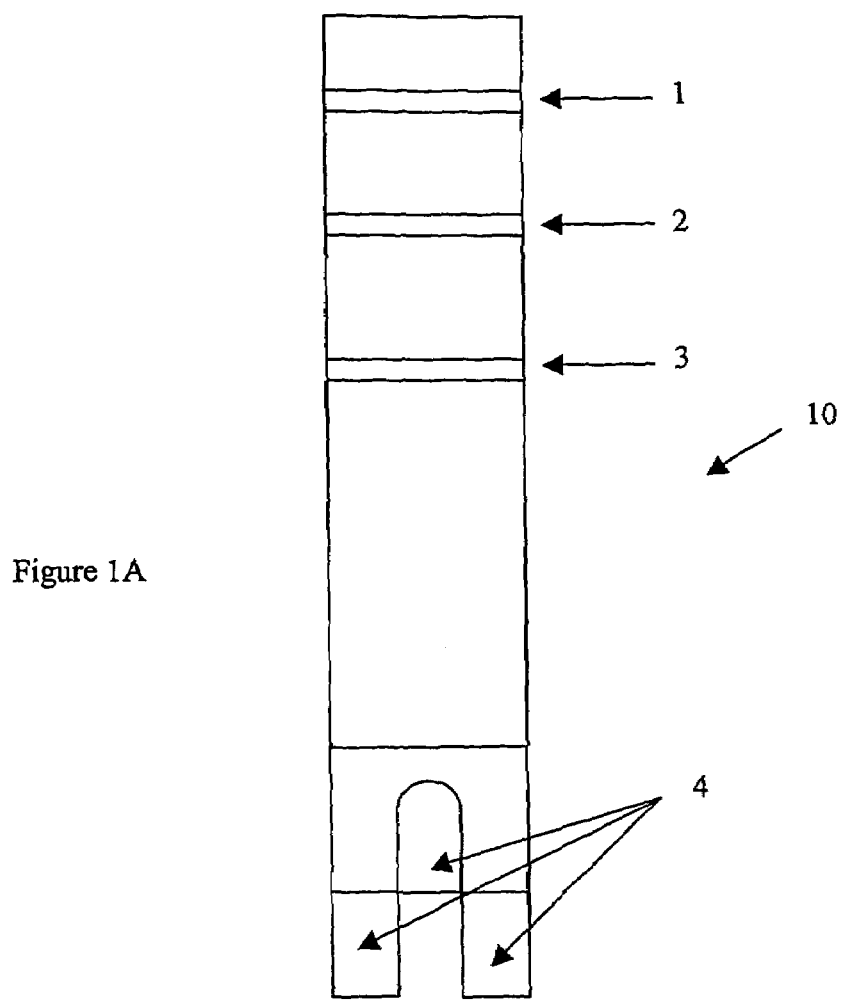
FIGS. 1A and 1B show a multi-cell apparatus of a preferred embodiment.

Embodiments of the invention are based upon the fact that electrochemical measurements, and in particular chronoamperometric measurements, can yield information about the concentration and/or the diffusion coefficient of electroactive species in solution. This is achieved by applying a potential between a working and counter (or counter/reference) electrode sufficient to produce a current proportional to the concentration of the reduced or oxidised form of an electroactive species being measured at the working electrode surface via the oxidation or reduction of the species at the electrode.

In many embodiments, this involves applying a potential sufficient to maintain the concentration of the electroactive species at zero at the working electrode surface.

The current that flows as a result of the reduction or oxidation occurring at the working electrode is related to the rate of mass transport which in this case is a product of the concentration gradient and diffusion coefficient. The current can be analysed to yield a measure of the concentration of the electroactive species, the diffusion coefficient of the electroactive species in the solution or both. For example, if the concentration of the electroactive species is known, then for an isolated working electrode the current can be analysed via the Cottrell equation or the like to yield a measure of the diffusion coefficient. The well-known Cottrell equation defines a relation between diffusion-limited current density and time. The diffusion current density is inversely related to the square root of time, or expressing it differently: the product of $i(t) \times t^{0.5}$ is a constant. The constant is proportional to the concentration of the reactant and to the square root of the diffusion coefficient of the reactant. On the other hand, if the diffusion coefficient of the species in the liquid sample is known, then the concentration can be inferred.

In another type of amperometric cell, a thin-layer cell, disclosed in the U.S. Pat. No. 6,284,125 the working and counter electrodes are placed relatively close to each other. In this case both the electroactive species diffusion coefficient and concentration can be measured without prior knowledge of either parameter.

It is not required in all embodiments that the potential of the working electrode be set such that the concentration of the electroactive species at the working electrode is maintained at zero (ie. the normal diffusion limited regime). It is only necessary that the current flowing be at least in part determined by the mass transport of species to the electrode. For example, the potential of the working electrode could be set such that for a particular rate of mass transport of the electroactive species to the electrode, the balance between the amount of electroactive species reacted at the electrode and the amount arriving at the electrode via mass transport resulted in the concentration of the electroactive species at the electrode being maintained at say 50% of the bulk concentration of electroactive species. Then, if the mass transport of the electroactive species to the electrode decreased due to barrier formation within the sample the balance would be shifted to the point where the concentration of electroactive species at the electrode was say 20% of the bulk concentration. The current flowing at the electrode would then change, as indicated by the Butler-Volmer equation and thus signal the change in sample barrier formation.

It is not necessary to use voltages that produce a direct current to carry out the measurements, voltages that produce an alternating current can also be used. For example a square-wave or sine-wave voltage can be applied. A typical amplitude and frequency for the voltage wave is 30 mV at a frequency of 5 Hz. This is particularly advantageous if one of the electrodes between which the voltage is being applied is coated with reagents which can undergo barrier formation and the second electrode has no such reagents present. In this case the asymmetry in the current signal can be used as a robust measure of any barrier formation occurring.

In embodiments of the present invention a measure of a barrier to restrict or reduce movement of the electroactive species is then derived from at least one of the measured current, the measure of concentration or the diffusion coefficient as explained in more detail below. Typically, the method is used to measure a barrier formed by an agglutination reaction. However, a barrier may also be formed in other circumstances. For example, a barrier may be formed by other clumping reactions, by a reaction that immobilises the electroactive species or by a reaction that binds the electroactive to a slower moving species.

Persons skilled in the art will appreciate that while embodiments of the present invention employ amperometric techniques, coulometric techniques may also be used to obtain a measure of barrier formation—ie. charge passing through the working electrode may be measured instead of current (usually, by measuring the current over time and integrating it to obtain the charge).

Amperometric cells of embodiments of the present invention require at least two electrodes, a working electrode a counter electrode, which are in contact with the liquid sample when the cell is filled. There can also optionally be a third electrode, the reference electrode whose purpose is to provide a reference potential against which the potential of the working electrode can be compared. In practice a reference is often not required at all or the counter electrode can be such that it functions as a reference electrode as well as the counter electrode. Herein, except where the context implies otherwise, the term "counter electrode" encompasses both separate counter electrodes and counter/reference electrodes.

At least the working electrode is required to be made of materials that are inert to chemical or electrochemical oxidation or reduction under the conditions of use. For example if a working electrode is to be used as an anode it must be inert to oxidation, either chemical or electrochemical, at the potential and in the chemical environment at which it is used. If a working electrode is to be used as a cathode then it must be inert to reduction, either chemical or electrochemical, at the potential and in the chemical environment in which it is to be used. Examples of materials suitable for use in an anode are gold, platinum, palladium, iridium, graphitic carbon, indium oxides, tin oxides, mixed indium/tin oxides, stainless steel, mercury. Mixtures or alloys of these materials are also suitable. Examples of materials that are suitable for use in a cathode are all of those listed above as suitable for an anode plus for example copper, steel, nickel, aluminium, chromium, and silver.

In all embodiments of the invention, a subject component, a testing component and at least one electroactive species are provided within the cell in order to obtain a measure of barrier formation.

Herein, the term "subject component" is used to refer to the subject of the barrier formation test—that is, the component with unknown properties. Typically, the subject component will be provided to the cell as part of a liquid sample which is to be tested for barrier formation. The sample may also be held within a porous gel or microporous membrane. However, persons skilled in the art will appreciate that the situation can be reversed—ie. that the "subject component" can be subjected to testing to determine its ability to cause barrier formation.

Similarly, the term "testing component" is used to refer to the component which has known properties and is used for testing the subject component. The testing component will usually be present in the cell before the liquid sample containing the subject component is introduced. However, it may also be added to the liquid sample before or after the liquid sample is provided to the cell.

The "electroactive species" is the species which exchanges electrons at the working electrode to cause an electrical current to flow in the cell.

The electroactive species may be provided as a product of the barrier formation reaction between the testing and subject components. Alternatively, it may be introduced separately to the liquid sample (or indeed to the cell itself).

The term "target component" is used to refer to the component which will react with the testing component and which may or may not be present in the subject component.

The term "agglutination" is used herein in its broadest sense and refers to a process of clumping of agglutinatable species comprising binding sites after exposure to an agglutinin. An agglutinin is a substance capable of interacting specifically with the binding sites on more than one agglutinatable species and thereby crosslinking the agglutinatable species, typically into a lattice-like configuration. By selecting agglutinins with binding specificity for a particular desired analyte, it is possible to detect the presence of the desired analyte within a mixture of compounds.

Agglutination reactions typically require the matching of concentrations of agglutinatable species and agglutinin. Excess agglutinin will saturate the binding sites on the agglutinatable species without allowing the formation of crosslinks between agglutinatable species. Excess agglutinatable species will rapidly bind up the agglutinin and reduce the likelihood of crosslinking between agglutinatable species. A person of skill in the art will readily be able to determine the optimal conditions for a specific agglutination reaction.

The agglutination reaction can be used to detect the presence of agglutinatable species binding sites, for instance a blood group antigen on the surface of a red blood cell, by providing an agglutinin to the desired antigen, or to detect the presence of an agglutinin, for instance circulating antibodies to a cell surface marker, by providing the appropriate agglutinatable species. Accordingly, depending on the application, the "subject component" may be an agglutinin and the corresponding "testing component" may be an agglutinatable species, or alternatively the "subject component" may be an agglutinatable species and the corresponding "testing component" an agglutinin.

Species suitable for agglutination reactions may include particulate carriers which are be coated with a specific binding site species, such as latex micro-beads, colloidal gold particles, charcoal particles or red blood cells to which an antigen has been absorbed on their surface. Other suitable carriers for the specific binding site species are polymers that can be crosslinked or agglutinated to form a diffusion barrier in the electrochemical cell. These polymers may be soluble or insoluble in the sample matrix. For aqueous samples for instance examples of suitable insoluble polymers are polystyrene, polycarbonate, polysulfone. Preferably these polymers would be in the form of micro filaments. Suitable soluble polymers for aqueous samples include poly acrylic acid, poly vinyl alcohol, poly vinyl sulfate, poly ester sulfonate, poly styrene sulfonate and poly styrene containing quaternary ammonium groups. Ideally such particles or polymers are readily suspended in solution. Another class of suitable carrier for the specific binding site is small molecules wherein the presence of the target species crosslinks the small molecules to form a larger species that is capable of retarding the movement of the electroactive species. An example of such a system is where sodium deoxycholate is the small molecule species, the specific binding sites are the carboxylic acid groups which make up part of the deoxycholate and the target species is calcium which serves to crosslink the deoxycholate. Alternatively, the agglutinate species may inherently express the antigen on their surface, for instance blood group antigens expressed on the surface of red blood cells or surface antigens expressed on microorganisms such as bacteria or fungi or virus particles.

An agglutinin is a molecule capable of binding two or more agglutinate species, preferably on different particles to enable the cross-linking between particles and subsequent lattice formation. Agglutinins typically include immunoglobulins, particularly IgM and IgG immunoglobulins. Such immunoglobulins may be polyclonal antibodies from sera or monoclonal antibodies produced in tissue culture, ascites fluid or by recombinant techniques. Polyclonal antibodies or a mixture of different monoclonal antibodies may be used to bind different antigenic epitopes on the same particle. Synthetic molecules which contain immunoglobulin amino acid sequences, such that the molecules possess the desired antigen-binding specificity are also contemplated. The skilled addressee will recognise that artificial antibody variants having the antigen-binding specificity of an antibody would also be able to participate as an agglutinin in agglutination reactions. Such variants include chimeric molecules having two or more antigen-binding sequences. The antigen-binding sites of such chimeric molecules may have the same antigen-binding specificity, or may have different antigen specificity. The skilled addressee will recognise that a chimeric molecule could contain binding sites from antibodies or other molecules such as lectins, or both. Other molecules with antigen-binding specificity may also be used as agglutinins. Lectins, for instance, demonstrate specificity in binding to terminal carbohydrate residues, and these may be used as agglutinins either in their unmodified form or when modified, for example by creating dimers or other oligomers or chimeric polypeptides having multiple binding sites so that they are capable of interacting with the surface of more than one antigenic particle at any one time.

According to one embodiment of the present invention the current flowing in the amperometric cell is used to obtain a measure of the barrier formation that has occurred in the liquid sample. The magnitude of the current flowing can be used to assess the presence of degree of barrier formation. For example, for particular volumes of subject and testing components, current flowing in the cell can be calibrated to barrier formation values using experimental data. The change in the magnitude of the current with time can also be used to obtain a measure of the diffusion coefficient of an electroactive species in the sample or the change in the diffusion coefficient of the electroactive species over time to thereby obtain a measure of barrier formation.

The change in magnitude or the ratio of magnitudes can be used to determine whether the barrier formation has taken place and/or to obtain a measure of the amount of barrier formation. Again, these measurements can be calibrated for particular subject and testing components. The difference in barrier formation spatially in the electrochemical cell can also be obtained. For example by coating a testing component in the form of barrier formation reagents over or near to one electrode in the cell, but not over a second electrode in the cell, the current passed with and without barrier formation could be assessed. In one embodiment of this aspect of the invention the potential of one electrode could be set such that it was the working electrode in the cell and the current flowing measured. The potentials between the electrodes could then be adjusted such that a second electrode became the working electrode, and again the current measured. If the sample above one of the working electrodes contained barrier formation reagents but the sample above the other working electrode did not then the currents between the two could be compared to assess barrier formation. This embodiment has the advantage of allowing for variations in the sample matrix and ambient test conditions that might otherwise affect the assessment of the barrier formation. This embodiment may also be used to detect the presence of barrier formation, in particular agglutination, of different species within a single amperometric cell. Such an application could include, for instance the determination of A, B, and Rh antigens on a single sample of human red blood cells using three working electrodes coated with either anti-A, anti-B or Rh antibodies.

In a particularly preferred embodiment of this aspect of the invention an electrode configuration is used where two electrodes are placed facing each other. According to this embodiment a testing component containing barrier formation reagents is coated onto one of the facing electrodes and a testing component containing no barrier formation reagents are coated onto the other facing electrode. The electrode with no barrier formation reagent would be made the working electrode first and the current flowing measured while the other electrode acts as the counter electrode. The polarity of the potential would then be reversed such that the other facing electrode became the working electrode and its current, in the presence of barrier formation reagents measured. An advantage of this embodiment is that the electrode layers can be coated with testing components separately, allowing for easy manufacture and a low chance of cross-contamination of the testing components. For this embodiment to work the electroactive species must be bound to the barrier formation reagent. Persons skilled in the art will appreciate that the binding reaction will strictly be one of immobilisation rather than agglutination. In this embodiment, the testing component and the electroactive species are the same and the subject component causes the electroactive species to be immobilised. Typically, such an embodiment will require one molecule of analyte per electroactive molecule immobilised, so it would only be applicable to higher concentration analytes.

In another particularly preferred embodiment of this aspect of the present invention the two facing electrodes referred to above are placed such that products of the counter electrode reach the working electrode during the test, such as in thin-layer cell of the type disclosed in U.S. Pat. No. 6,284,125, the disclosure of which is incorporated herein by reference. In cells such as those disclosed in U.S. Pat. No. 6,284,125 the diffusion coefficient can be measured substantially independently of the working electrode area being used or the concentration of electroactive species present. By alternately using each facing electrode as the working electrode, one without barrier formation reagent coated onto it and one with barrier formation reagent coated onto it, and analysing the current flowing in each case to yield a diffusion coefficient, a more direct measure of the barrier formation occurring can be obtained which is less dependent upon fabrication errors, where an electrode may not have the assumed area or user errors such as the user only partially filling the cell with sample.

In another embodiment of this aspect of the present invention only one electrode would be used as the working electrode during the test. According to this embodiment the current flowing at the working electrode would be measured at a suitably short time after the sample had been introduced into the sensor cell and compared to the current flowing at least one longer time after the sample was introduced into the sensor cell. A suitably short time is a time before which a significant amount of barrier formation would be expected to have occurred in the cell in the presence of the target component. A suitably longer time is one where a significant amount of the barrier formation reaction would be expected to have occurred in the cell in the presence of the target component.

A time before significant barrier formation is expected to occur is a time when the change in the barrier formation measuring parameter is less than about 20% or more preferably less than about 10% of the total change in that parameter when the barrier is fully formed in the sample.

A time by which significant barrier formation is expected to occur is a time when the change in the barrier forming measuring parameter is more than about 50% or more preferably more than about 70% of the total change in that parameter when the barrier is fully formed in the sample.

In practice these times can be determined by considering the range of barrier formation kinetics possible over the range of samples and test conditions to which the device is to be applied and picking times suitable for the whole range. Alternatively, by assessing the rate of change of the barrier formation measuring parameter over time, suitable times can be obtained for each individual test.

As would be apparent to one skilled in the art the rate of change of the barrier formation measuring parameter itself could also be used as a measure of the presence or absence or concentration of the test species of interest.

By comparing the currents measured at the different times a measure of the barrier formation that has occurred can be obtained that is less dependent upon the sample matrix or the temperature at which the test is performed.

According to this embodiment, in the case where the working electrode is sufficiently far enough away from the counter electrode in the cell such that reaction products from the counter electrode do not reach the working electrode during the time of the test, the potential difference could optionally be applied between the electrodes for a short period to measure the current at a short time. It could then be switched off to allow the concentration gradients in the electroactive species to relax back. The potential difference between the electrodes would then be applied again at a longer time suitable for measuring the current at the longer time. In some cases this could lead to a more accurate measure of the barrier formation that had occurred.

Operating the invention according to this embodiment requires that the barrier formation reaction kinetics are such that they are slow enough to allow sufficient time to measure a current signal indicative of the liquid sample without significant barrier formation but fast enough such that the barrier formation reaction in the presence of the analyte would be completed in a desirably short time.

In some embodiments of the current invention the barrier formation, more specifically agglutination, that can occur in the cell is as a result of the reactions between an antigen or antigens and antibody or antibodies. The testing component could be either an antigen or antibody or the antigen or antibody could comprise part of the testing component with the target component being the other of the antigen or antibody.

In a preferred embodiment of this aspect of the current invention the testing component is of a suitable size and functionality such that it is capable of being suspended in the liquid sample without undue stirring but large enough such that it would cause a significant barrier to diffusion. Examples of suitable testing components are antigens or antibodies bound to a polymer which is soluble in the sample liquid, or bound to small insoluble beads or fibres. Examples of suitable soluble polymers are poly(acrylic acid), poly(vinyl sulphate), poly(styrene sulphonate) and poly(vinyl alcohol). Examples of materials suitable for use for the insoluble beads or fibres are polystyrene, latex or poly(acrylamide). Alternatively, antigen or antibody may be on the surface of cells, such as red blood cells or bacterial cells in suspension.

It is not always necessary for the testing component to be large enough to cause a significant barrier to diffusion itself. For example if the target component were of sufficient size to cause a significant barrier to diffusion the testing component could be quite small. An example of such a target component is antigens on the surface of cells, where the testing component is an antibody to the cell surface antigens and causes the cells to agglutinate. In the case of cells or other particles suspended in the sample prior to its introduction into the cell being the agglutinating particles, the particles need only be of a suitable size and/or density such that they will not substantially settle in the cell during the test, at least in the non-agglutinated form.

In another embodiment of this aspect of the present invention the testing component may be a species that is capable of binding to a relatively large particle such as a cell as well as binding to the target component. Further, according to this embodiment the target component would be capable of binding more than one testing component such that, by binding at least two testing components, and wherein each testing component is also bound to a separate particle, the particles would form a barrier.

In some embodiments a testing component for processing the liquid sample is dried into the electrochemical cell. The testing component could be dried in contact with at least one electrode of the cell or on an inert wall of the cell. Alternatively the testing component could be dried outside the cell in a place such that the sample came into contact with and dissolved the testing components before being introduced into the electrochemical cell. The testing component could comprise an electroactive species or species that formed an electroactive species when it(they) came into contact with the liquid sample. Alternatively, the electroactive species could already be present in the sample to be tested. The electroactive species could be at a known concentration, however this is not necessarily required for some embodiments of the present invention to function in some embodiments. For example, if the diffusion coefficient of the electroactive species was measured using thin-layer cells as previously described the measurement is substantially independent of the concentration of the electroactive species present. Similarly, if a comparison of current signals is to be made then the comparison will often be independent of the concentration of electroactive species present. The electroactive species must be soluble and mobile in the sample. Examples of suitable electroactive species are $Fe(CN)_6\ 3-$, $Fe(CN)_6\ 4-$, $Cr3+$, $Cr2O7 2-$, $Cu2+$, $Co(NH_3)_6 3+$, $Co(NH_3)_6 2+$, $Sn4+$, $I-$, $Br-$.

As well as this electroactive species the testing component may also contain the soluble redox conjugate oxidant or reductant to the electroactive species or a second soluble electroactive species where this species is required to complete the electrochemical circuit by reacting at the counter electrode. Preferably this second electroactive species would be in excess relative to the first electroactive species such that it did not limit the current flowing in the electrochemical cell. In other configurations the counter electrode may complete the circuit by oxidising or reducing an insoluble species as is known in the prior art. Examples of materials suitable for such counter electrodes are silver/silver chloride, silver/silver bromide, mercury/mercurous chloride, mercury/mercurous sulphate.

Optionally the testing components may also contain a buffer for controlling pH and stabilizing the reagents and other additives designed to aid manufacturing and usability aspects of the sensor. For example surfactants and polymers may be added to improve how the dried reagents are formed during manufacture and/or improve the way the cell fills with sample, for example by modifying the hydrophilicity of the surfaces of the cell. Examples of suitable buffers are phosphates, carbonates, borates, citraconate, citrate and mellitate. Examples of suitable surfactants are Triton X-100, tween, Brij 35, Brij 20 pluronics. Note that when the liquid sample or cell testing components to be used contain proteins the surfactant should be such that it does not denature the proteins in a way that could interfere with the test. Also, in situations where there is an oxidant in the testing components that is capable of oxidising haemoglobin the surfactant should not lyse the red blood cells as the liberated haemoglobin may be oxidised and interfere with the sensor current signal. This criterion is less important however in embodiments where the measure of agglutination is substantially independent of the concentration of the electroactive species present.

In a preferred embodiment for using the present invention a sample of liquid to be tested for the target component is introduced into a cell containing at least two electrodes, a working electrode and a counter or counter/reference electrode, and dried testing components. Upon filling the cell the liquid sample at least partially dissolves the dried reagents and if the target component is present the testing component and the target component interact to form a barrier of species in the liquid. The barrier formation occurring is monitored by measuring characteristics of the current flowing between the electrodes in the cell. In order for current to flow between the electrodes a potential difference is applied between the working and counter electrodes where the potential difference is sufficiently large to cause an electrochemical oxidation or reduction reaction to occur at working electrode/solution interface and a corresponding reduction or oxidation reaction to occur at the counter electrode/solution interface. Furthermore, the potential difference between the electrodes should be high enough to maintain the concentration of the species being oxidised or reduced at the working electrode/solution interface at effectively zero. Barrier formation measurement means, typically completes the apparatus for determining a measure of barrier formation from the current.

As discussed above, in another embodiment of the invention one or more of the testing components could be present in the liquid sample or added to the liquid sample prior to the liquid sample being introduced into the cell.

In other embodiments, the liquid sample may be a porous gel, such as an agarose gel in which the barrier formation reaction takes place. Another possibility is that the barrier formation reaction occurs within a microporous membrane onto which an electrode is coated. These configurations might make the use of beads coated in the barrier forming agent easier as the beads could be suspended in the pores and block them if the barrier is formed, thus removing the requirement that the beads have to be readily suspendable in the sample.

In some embodiments more than one electrochemical cell are incorporated into a single device to allow the measurement of multiple barrier formation reactions with one device.

In one embodiment of this aspect of the invention the separate electrochemical cells could be formed such that at least some of the working electrodes in the separate cells could be separately connected to an external electrical circuit. In this way the current flowing at the separately connected working electrodes could be separately monitored. Alternatively, the electrochemical cells may be provided as a microarray or other known structure for providing a plurality of testing components.

In a preferred embodiment of this aspect of the present invention the working electrodes in the separate electrochemical cells are arranged such that they all connect to a current measuring circuit via the same connections. This is particularly preferred when the cells are designed for a single use and then to be disposed of. For example the device could be a strip containing the multiple cells that is inserted into a meter, used to analyse a sample and then the strip discarded. In such single use devices it is desirable to keep the cost of supplying the strip to the user and the complexity of the meter low. Therefore a strip with fewer connections to the meter is preferred.

An example of the method of use of this embodiment of this aspect of the present invention is that sample would be introduced into a first cell and current measurements indicative of the agglutination occurring obtained such that at the end of this portion of the test the current in the first cell is known and can be predicted at longer times.

A second cell could then be filled with sample and second current measurements made that were indicative of barrier formation occurring in the second cell. In order for the current in the second cell to be accurately measured the current known to be flowing in the first cell would be subtracted from the total current flowing. After the measurement of barrier formation occurring in the second cell was completed, if further cells on the same device were to be used, the current flowing in the first and second cells need to be in a known state such that they can be subtracted from the current flowing when the third cell is filled, and so on.

In a preferred embodiment of the multi-cell device the cell would be a thin-layer electrochemical cell so that after a suitable time the current flowing in any of the previously filled and barrier formed cells is substantially constant, allowing more accurate subtraction of currents flowing in previously filled cells from that flowing in the latest cell filled.

To illustrate aspects of the present invention an example of an application for determining blood type is given. In this application it is usual to obtain the presence or absence of three antigens on the surface of red blood cells to type the blood. The antigens are A-antigen, B-antigen and Rh-antigen.

According to the embodiments of the invention the required measurements could be made with three separate devices or, more preferably by a single device with three cells on the same device termed here a strip. In the case of cells on separate strips, or on the same strip, one cell would contain a first testing component in the form of an antibody to the A-antigen, a second cell would contain an antibody to the B-antigen (a second testing component) and the third cell an antibody to the Rh-antigen (a third testing component). In use the strip would be inserted into a meter that had a connection device that connected the strip electrodes to an electrical circuit. The electrical circuit would be completed by an electrical power source capable at least of applying the desired potential between the electrodes and measuring the resulting current. In a preferred embodiment, the meter also includes an agglutination measurement means which has the ability to analyse the measured current signals, display a result, store results and interface with other equipment. The agglutination measurement means may be a modified ammeter. The meter may include a sampling means for extracting current measurements at desired times.

In this example the electrodes in the cells would be placed facing each other and approximately 100 microns apart. Reagent comprising 10 mM potassium ferrocyanide would be coated onto the upper electrode in all three cells and reagents comprising 100 mm potassium ferricyanide and antibody coated onto the lower electrode. The antibody is to A-antigen in the first cell, B-antigen in the second cell and Rh-antigen in the third cell.

In use, the user fills the first cell with a sample of whole blood (the subject component) and a potential of 300 mV is applied between the electrodes such that the upper electrode is the anode and thus the working electrode and the lower electrode the cathode and thus the counter electrode. The current is recorded and the current after a few seconds compared to the current recorded at a long enough time that any agglutination reaction should have taken place. By having no agglutination reagent on the working electrode the onset of the agglutination reaction near the working electrode is delayed, allowing sufficient time to record a current indicative of the non-agglutinated sample. If the ratio of the current measured at long times to that measured at short time is less than a pre-determined threshold value then the presence of the A-antigen (the target component) is detected.

Once a suitable time has elapsed for the detection of the A-antigen in the sample in the first cell if present, the meter would indicate to the user to fill the second cell with another sample of the same blood. Note that by this time the current in the first cell is either a steady value or changing with time in a predictable manner. Once the user fills the second cavity with sample a second current trace is recorded which corresponds to the total current flowing in the first and second cell. The meter then subtracts the known current from the first cell to arrive at a current for the second cell. As before, this current is examined at short times and at longer times to detect if agglutination is occurring.

After an appropriate time for the detection of B-antigen in the second cell the meter instructs the user to fill the third cavity with another sample of the same blood and the known currents in the first and second cells subtracted from the total current to give the current in the third cell. The current is examined as above to detect if agglutination is occurring.

From the three results the blood types A, B, AB and O can be ascertained as well as whether the blood being analysed is Rh positive or negative.

Note that the blood sample could be capillary, venous or arterial.

PREFERRED EMBODIMENT OF THE INVENTION

Figure 1B:
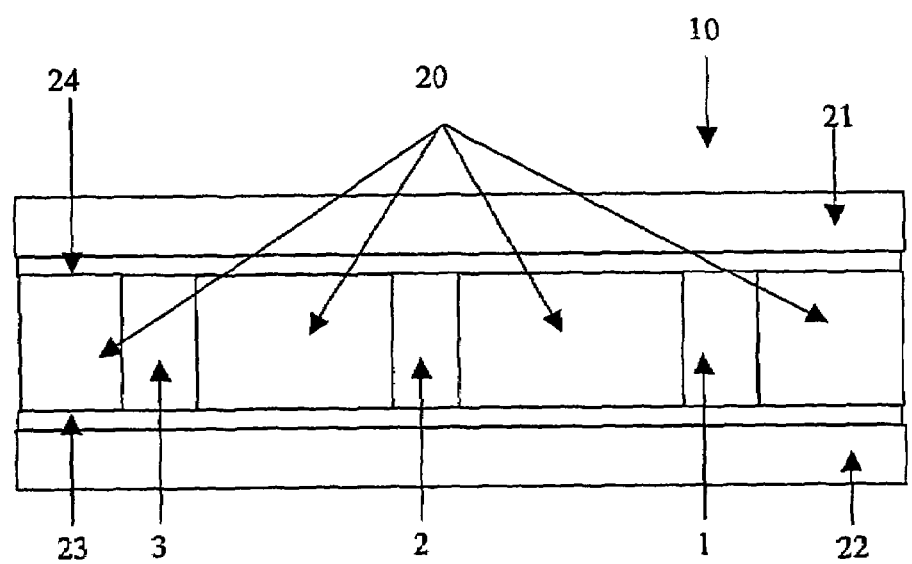

A suitable multi-cell strip is illustrated in FIGS. 1a and 1b. FIG. 1a shows a top view of the device, FIG. 1b shows a cross-sectional view (not to scale) of the device.

The strip 10 has cells 1, 2 and 3 formed in it by cut-outs in an insulating spacer layer 20 interposed between upper and lower layers 21 and 22, which have electrode layers 23 and 24 coated onto their inner surfaces. Connection points 4 are provided to connect the electrode layers to an external electrical circuit in a meter (not shown). An appropriate circuit for carrying out the necessary measurements can readily be devised by a person skilled in the art. Testing components (not shown) are dried onto the inner surface of layers 23 and 24 in registration with the cavities 1, 2 and 3.

EXAMPLES

Example 1

An agglutination Sensor for Calcium

An agglutination sensor for calcium is developed as a model for determining the efficiency of the present invention.

Gold electrodes were prepared by sputtering a 30 nm thick gold coating onto 0.007" thick Melinex 453®.

A solution consisting of 44 mg/mL sodium deoxycholate, 214 mM potassium ferricyanide and 0.11% Pluronic PE6200 was prepared in 27% ethanol/1.5% isopropanol/71.5% water. This solution was coated onto the gold electrode and dried.

A rectangular hole was cut out of a 107 μm thick double sided adhesive tape. The tape was laminated to the gold electrode in such a way that the hole overlaid the dried chemistry. A second gold electrode coated with the above reagents was laminated to the other side of the tape, thus forming an electrochemical cell with opposing electrodes. The trilaminate was cut in such a way that the area of the electrode was well defined (0.0985 cm$^2$), and there were openings at the ends of the rectangular hole that served as a sample entry port and air exit vent for filling the sensor.

Figure 2:
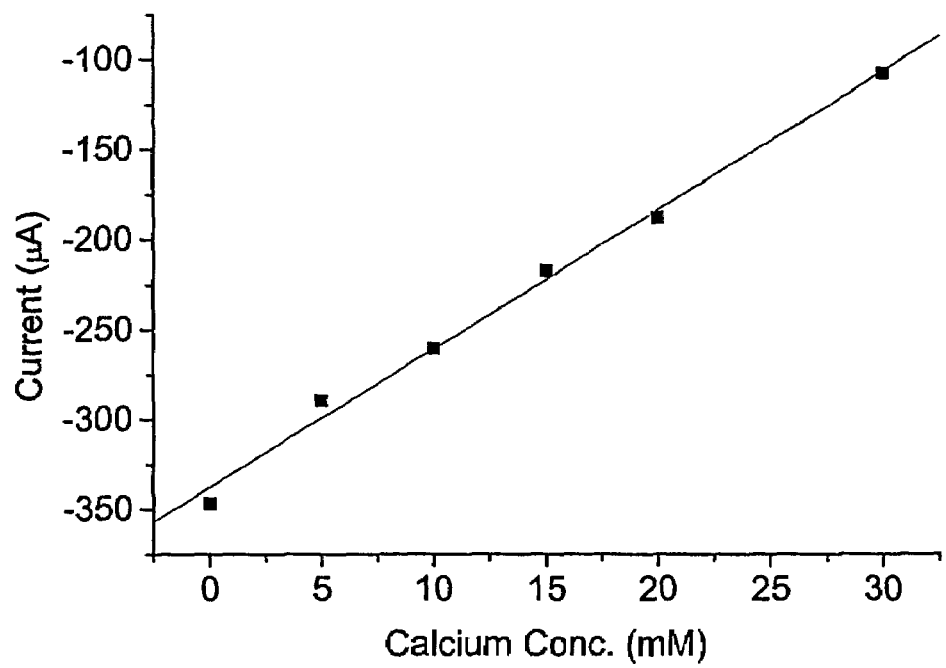
FIG. 2 is a graph of current for the differing calcium solutions of Example 2.

The two electrodes were attached to a potentiostat and a solution of 9 mM potassium ferrocyanide containing 0-30 mM CaCl$_2$ was loaded into the electrochemical cell. A potential of −0.3 V was applied for 25 seconds and then +0.3 V was applied for 10 seconds. The current was measured at 0.1 seconds after +0.3V was applied. The current for the various calcium containing solutions is shown in FIG. 2.

Example 2

Sensor for the Proteolytic Activity of Rennin

A separate type of agglutination reaction was provided by the action of the enzyme rennin on milk. Rennin cleaves a hydrophilic phosphorylated peptide off casein in milk to generate an insoluble protein. This protein then agglutinates and can form yoghurt or cheese after further processing.

A sensor for rennin would be provided by drying down milk or casein mixed with an electroactive species in an electrochemical cell. If a liquid introduced into the cell contains active rennin then the ensuing agglutination can be sensed by applying a voltage between the electrodes and analysing the current transient.

Example 3

The enzyme assay described in Example 2 can be used in an immunoassay which is carried out in a single chamber, involves no washing steps, and does not have a fixed timing step.

Figure 3:
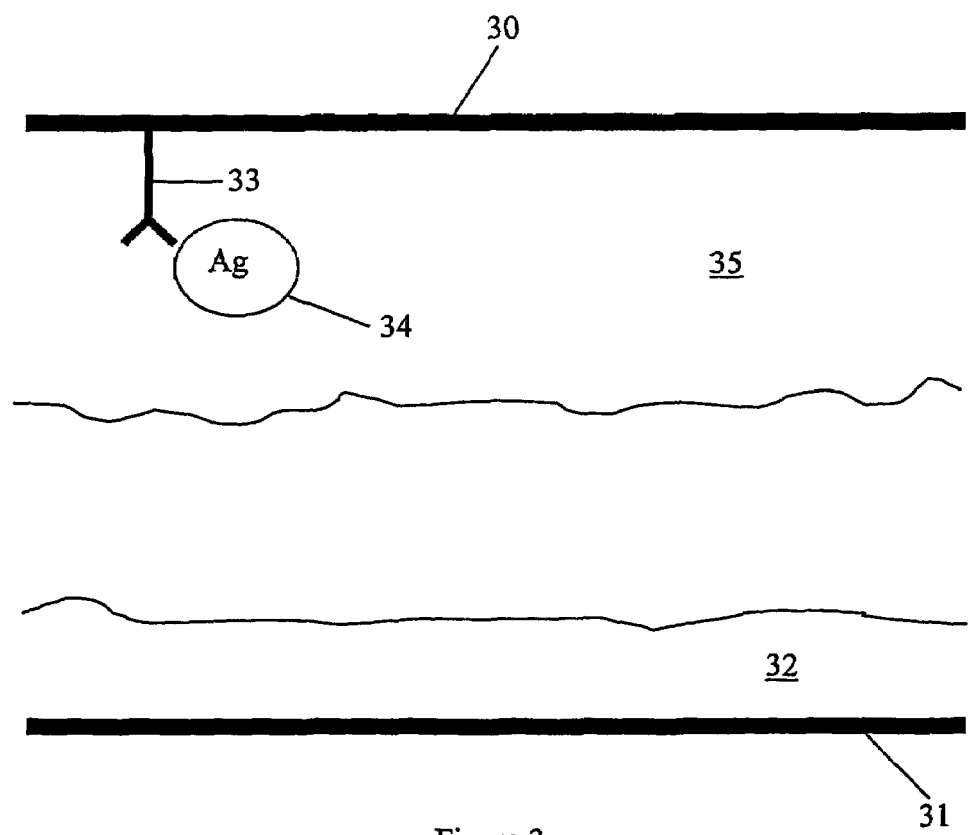
FIG. 3 shows the immunosensor of Example 3.

The features of this immunoassay are shown in FIG. 3. The sensor consists of a single chamber with an upper surface 30, which may be an electrode or a plain polymer or other surface and a lower electrode 31. The lower electrode 31 has a coating of casein (milk protein). The upper surface 30 has a coating of immobilized antibodies 33 (shown as the Y-shaped structure), with antigen-rennin 34 conjugates non-covalently bound to the antigen binding sites on the antibody to form an antibody-antigen-rennin layer. A mixture of an oxidised and reduced form of a redox couple, for example a mixture of ferricyanide and ferrocyanide is coated onto the lower and/or the upper electrode/surface.

When a fluid with an unknown concentration of the antigen is introduced into the chamber, the free antigen can "compete off" the bound antigen-rennin conjugates. The conjugates then diffuse down to the casein layer and initiate coagulation of the casein forming a barrier layer next to the lower electrode 31. The process of agglutination can be followed continuously by applying a fixed voltage and monitoring the current, or the diffusion coefficient of reduced or oxidised redox species can be monitored at various times by applying a voltage pulse sequence as described elsewhere in this application, or the polarity of the voltage can be reversed rapidly and the peak currents can be monitored with time. The magnitude and optionally the rate of change of the current flowing at the lower electrode will correspond to the extent of agglutination proceeding with time, which in turn will be proportional to the amount of antigen-rennin conjugates that reaches the casein layer. This in turn will be proportional to the concentration of antigen that was in the sample solution.

It will be apparent to the person skilled in the art that various modifications may be made to the present invention and these should be considered as falling within the scope of the invention described herein.

The invention claimed is:

1. A method of measuring formation of a barrier to restrict or reduce movement of an electroactive species, the method comprising:
   providing an electrochemical cell having a working electrode and a counter electrode spaced from the working electrode;
   providing a subject component, a testing component and at least one electroactive species within the cell, the subject and testing components being intended to cause the formation of a barrier by an agglutination reaction to restrict or reduce movement of an electroactive species;
   applying a DC potential to the electrochemical cell between the working electrode and the counter electrode sufficient to produce a current related to the rate of mass transport of the electroactive species being measured to the working electrode; and
   measuring the current at the working electrode to obtain a measure of the formation of the barrier to restrict or reduce movement of the electroactive species.

2. A method as claimed in claim 1, wherein the subject and testing components are intended to form a barrier by an agglutination reaction.

3. A method as claimed in claim 1, wherein the applied potential is sufficient to maintain the concentration of the electroactive species at the working electrode.

4. A method as claimed in claim 1, wherein the step of measuring the current comprises measuring the current at a first time before significant barrier formation is expected to occur in the cell and measuring the current again at a second time by which significant barrier formation is expected to occur, and obtaining said measure of barrier formation from the difference in measured current.

5. A method as claimed in claim 4, comprising selecting the first time to be a time when the change in a barrier formation measuring parameter is or is expected to be less than about 20% of the total change in that parameter when the barrier is fully formed.

6. A method as claimed in claim 5, wherein the change in barrier formation measuring parameter is less than about 10% of the total change.

7. A method as claimed in claim 4, comprising selecting the second time to be a time when the change in the barrier formation measuring parameter is or is expected to be more than about 50% of the total change in that parameter when the barrier is fully formed.

8. A method as claimed in claim 7, wherein the change in barrier formation measuring parameter is more than about 70% of the total change.

9. A method as claimed in claim 4, comprising selecting said first and second times by assessing the rate of change of the barrier formation measuring parameter over time.

10. A method as claimed in claim 1, wherein the difference in measured current is used to obtain a measure of the diffusion coefficient of the electroactive species to thereby obtain a measure of barrier formation.

11. A method as claimed in claim 1, wherein the difference in measured current is used to obtain a measure of the change in diffusion coefficient to thereby obtain a measure of barrier formation.

12. A method as claimed in claim 1, wherein the step of providing the subject component is performed by introducing a liquid sample containing the subject component into the cell.

13. A method as claimed in claim 12, wherein the step of providing the testing component is performed by introducing the testing component to the liquid sample before the liquid sample is introduced in the cell.

14. A method as claimed in claim 12, wherein the step of providing the testing component is performed by introducing the testing component into the cell before the liquid sample is introduced.

15. A method as claimed in claim 14, wherein the testing component is introduced to the cell by drying the testing component into the cell.

16. A method as claimed in claim 1, comprising providing said electroactive species by means of a reaction between the testing component and the subject component.

17. A method as claimed in claim 1, comprising providing said electroactive species by means of the testing component.

18. A method as claimed in claim 1, wherein the electroactive species is provided by the barrier formation reaction, the method further comprising providing two electrodes which can act as the working electrode and providing the testing component close to or at one of the two electrodes, the method further comprising varying the applied potential or current measuring circuit connections in order to switch between said working electrodes, and measuring the current at both working electrodes to thereby obtain a measure of barrier formation.

19. A method as claimed in claim 1, wherein the current is measured to obtain a measure of charge in order to obtain the measure of barrier formation.

20. A method as claimed in claim 1, wherein the subject and testing components are intended to cause formation of a barrier when said subject component comprises a target component, and wherein the method further comprises determining whether said target component is present from the measure of the formation of the barner.

* * * * *